United States Patent
Kersten et al.

(10) Patent No.: US 9,039,690 B2
(45) Date of Patent: May 26, 2015

(54) COMBINED ULTRASOUND AND HF SURGICAL SYSTEM

(75) Inventors: Lutz Kersten, Berlin (DE); Timo Strauβ, Berlin (DE); Stefan Schiddel, Potsdam (DE); Uwe Fischer, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 504 days.

(21) Appl. No.: 13/392,720

(22) PCT Filed: Sep. 10, 2010

(86) PCT No.: PCT/EP2010/063291
§ 371 (c)(1),
(2), (4) Date: Feb. 27, 2012

(87) PCT Pub. No.: WO2011/032891
PCT Pub. Date: Mar. 24, 2011

(65) Prior Publication Data
US 2012/0165816 A1    Jun. 28, 2012

(30) Foreign Application Priority Data
Sep. 15, 2009 (DE) .......................... 10 2009 041 329

(51) Int. Cl.
*A61B 18/04* (2006.01)
*A61B 18/12* (2006.01)
(Continued)

(52) U.S. Cl.
CPC ..... *A61B 18/1233* (2013.01); *A61B 17/320092* (2013.01); *A61B 2018/00589* (2013.01);
(Continued)

(58) Field of Classification Search
CPC .................... A61B 18/04; A61B 2018/00577; A61B 18/1492
USPC ...................................... 606/27, 1
See application file for complete search history.

(56) References Cited

U.S. PATENT DOCUMENTS

| 4,200,104 A | 4/1980 | Harris |
| 5,633,578 A | 5/1997 | Eggers et al. |

(Continued)

FOREIGN PATENT DOCUMENTS

| EP | 0 310 431 A2 | 4/1989 |
| JP | A-60-227748 | 11/1985 |

(Continued)

OTHER PUBLICATIONS

Dec. 3, 2010 International Search Report issued in International Patent Application No. PCT/EP2010/063291.

(Continued)

*Primary Examiner* — Christopher D Koharski
*Assistant Examiner* — Philip Edwards
(74) *Attorney, Agent, or Firm* — Oliff PLC

(57) ABSTRACT

The invention relates to a combined ultrasound and HF surgical system, including at least one ultrasound generator which operatively provides an excitation signal through which an ultrasound converter can generate an ultrasound vibration, at least one HF generator which operatively generates HF energy, and at least one ultrasound and HF instrument electrically connected with the HF generator and the ultrasound generator, wherein the ultrasound vibrations and the HF energy are introducible into biological tissue through the HF instrument which includes at least one ultrasound converter and at least one HF electrode. In order to be able to use HF energy and ultrasound energy simultaneously without damaging the instrument or wearing the it out, the system includes a protective device which prevents sparks operatively generated through HF energy or reduces the probability of occurrence of the sparks.

7 Claims, 6 Drawing Sheets

(51) Int. Cl.
*A61B 17/32* (2006.01)
*A61B 18/00* (2006.01)

(52) U.S. Cl.
CPC .......... *A61B2018/00601* (2013.01); *A61B 2018/00666* (2013.01); *A61B 2018/1213* (2013.01); *A61B 2018/00994* (2013.01)

(56) References Cited

U.S. PATENT DOCUMENTS

| | | | |
|---|---|---|---|
| 5,658,277 A * | 8/1997 | Marshall et al. | 606/34 |
| 6,142,992 A | 11/2000 | Cheng et al. | |
| 6,204,729 B1 | 3/2001 | Takita | |
| 6,328,703 B1 | 12/2001 | Murakami | |
| 7,137,980 B2 | 11/2006 | Buysse et al. | |
| 2001/0001314 A1 | 5/2001 | Davison et al. | |
| 2002/0002369 A1* | 1/2002 | Hood | 606/5 |
| 2003/0204185 A1* | 10/2003 | Sherman et al. | 606/41 |
| 2004/0167508 A1 | 8/2004 | Wham et al. | |
| 2008/0146921 A1* | 6/2008 | Novak et al. | 600/437 |

FOREIGN PATENT DOCUMENTS

| | | |
|---|---|---|
| JP | A-03-111036 | 5/1991 |
| JP | A-7-500514 | 1/1995 |
| JP | A-8-117242 | 5/1996 |
| JP | A-11-239032 | 8/1999 |
| JP | A-11-318919 | 11/1999 |
| JP | A-2002-306507 | 10/2002 |
| JP | A-2004-329930 | 11/2004 |

OTHER PUBLICATIONS

Dec. 3, 2010 Written Opinion of the International Searching Authority issued in International Patent Application No. PCT/EP2010/063291.
Office Action issued in Japanese Patent Application No. 2012-529220 dated Jan. 27, 2014.
Translation of Japanese Office Action issued in Japanese Application No. 2012-529220 mailed May 19, 2014.
Office Action issued in European Application No. 10751676.7 dated Jul. 25, 2013.
Translation of Oct. 14, 2014 Office Action issued in Japanese Application No. 2012-529220.

* cited by examiner

COMBINED ULTRASOUND AND HF SURGICAL SYSTEM

The invention relates to a combined ultrasound and HF surgical system, including at least one ultrasound generator which operatively provides an excitation signal through which an ultrasound converter can generate an ultrasound vibration, at least one HF generator which operatively generates HF energy, at least one ultrasound HF instrument electrically connected with the HF generator and the ultrasound generator, wherein the ultrasound vibrations and the HF energy are introducible into biological tissue through the HF instrument which includes at least one ultrasound converter and at least one HF electrode.

Surgical systems as recited supra are known in the art. Thus combined ultrasound and HF surgical instruments are described e.g. in U.S. Pat. No. 6,328,703 B1 through which instruments biological tissue can be treated with ultrasound vibrations and also HF (hi-frequency) energy. The ultrasound- and HF-instrument is operatively connected to an ultrasound generator and a HF generator. The ultrasound generator generates an alternating current with a frequency of e.g. 35-50 kHz during operations. The excitation current is conducted to an ultrasound convertor in the instrument, wherein the ultrasound converter converts the electrical energy into ultrasound vibration. The ultrasound vibration is transmitted in the instrument to an ultrasound applicator through which the vibrations can be introduced into human tissue. The HF generator generates high frequency AC power with a frequency of e.g. 300 kHz to 2 MHz This HF energy is also transmitted to the instrument. The instrument includes at least one HF electrode through which the HF energy can be introduced into the tissue. For instruments with only one electrode an additional neutral electrode is connected to the tissue and the HF generator, wherein the HF energy runs through the neutral electrode. For bipolar instruments with two electrodes no neutral electrode is required, since the HF energy herein flows from one electrode through the tissue to the other electrode. The HF energy can be used for coagulating e.g. for stopping bleeding. The ultrasound energy can be used for cutting tissue which has the advantage that the tissue does not stick to the instrument due to the ultrasound vibrations.

Ultrasound and HF energy should be used in the known systems in an alternating manner since simultaneous application can damage or destroy the combined instrument. Thus, the HF energy can damage e.g. a coating of the ultrasound applicator or also particular materials like e.g. Teflon. Unfortunately, the treatment time of the combined ultrasound and HF system is rather long due to the separate application of ultrasound and HF energy which leads to longer surgery times and thus to higher costs.

Thus, it is an object of the present invention to provide an improved combined ultrasound and HF surgical system in which the treatment time is shortened compared to prior art systems.

This object is accomplished for the combined ultrasound and HF surgical system recited supra in that the system includes a protective device which prevents sparks operatively generated by HF energy or reduces their probability of occurrence.

The solution according to the invention has the advantage that it eliminates the causes for damages at the instrument, namely the sparks. Thus, ultrasound and HF energy can be applied simultaneously, so that surgical times can be shortened.

The option to apply ultrasound and HF energy simultaneously allows developing completely new surgical procedures which were not possible up to now.

Preferred embodiment of the invention are describes infra.

It has become apparent that HF voltage has a substantial influence on spark generation. A damaging spark can be generated already through short term ($\Box$1 ms) electrical voltage peaks of the HF voltage applied between the HF electrodes. In a preferred embodiment of the invention the protective device can include a HF voltage limiter which prevents a HF voltage above a predetermined threshold voltage between a first HF electrode and a second HF electrode within a response time of less than 1 ms. Thus, the solution according to the invention prevents peak voltages within a time period which is shorter than 1 ms.

Thus voltage controllers are also known for prior art HF generators, wherein the voltage controllers control higher voltages to make them lower. However, these controls cannot prevent the generation of energy rich sparks because the sparks are created long before the control starts. In order to prevent voltage peaks which occur even in shorter intervals, the HF voltage limiter can prevent a HF voltage above the threshold voltage within a response time of less than 1 μs.

The voltage limiter can be located anywhere in the path of the HF energy.

In a preferred embodiment of invention the HF voltage limiter can include at least one TVS (transient voltage suppressor) diode. The known TVS diode has the advantage that when exceeding the threshold voltage, the HF voltage is only reduced to threshold voltage, but not completely turned off. Thus, the HF surgical application can be continued unimpaired. Each TVS diode is produced with a fixed threshold voltage. The threshold voltage of the HF voltage limiter can thus be adjusted through plural TVS diodes connected in series. Since the typical HF signals are alternating signals, preferably bidirectional TVS diodes are used. They provide voltage limitations in both directions. As an alternative to the TVS diodes the HF voltage limiter can also include a Varistor. Furthermore, the HF voltage limiter can include at least one switch which facilitates switching between two different threshold voltages. Thus, e.g. different numbers of TVS diodes can be connected. This has the advantage that different threshold voltages can be adjusted for different applications.

In order to tap the HF voltage where it determines spark generation, the HF voltage limiter can be electrically connected between the HF electrodes.

Besides the surgical system described supra the invention also relates to a HF generator for cutting and/or coagulating biological tissue. The HF generator includes at least two HF outputs with different polarity, wherein the HF electrodes of a surgical ultrasound HF instrument are connectable to the outputs, wherein the HF generator includes at least one ultrasound/HF operating mode in which a HF output energy optimized for the ultrasound/HF instrument is operatively provided at the HF outputs. In order to provide a HF generator which is improved for application of an ultrasound instrument, the HF generator includes a protective device. The protective device operatively prevents a spark of HF energy or reduces the probability of the spark.

In a preferred embodiment of the HF generator the protective device can include a HF voltage limiter which prevents a HF output voltage above a predetermined threshold voltage at the HF outputs within a response time of less than 1 ms.

The invention furthermore relates to a surgical device for providing an ultrasound energy signal and a HF energy signal for cutting and/or coagulating biological tissue. The surgical device includes an ultrasound generator which operatively provides an excitation signal through which an ultrasound generator can generate an ultrasound vibration, at least one ultrasound output connected to the ultrasound generator, wherein an ultrasound HF instrument is connectable to the ultrasound output, at least one HF energy input at which a HF generator for introducing a HF energy signal is connectable and at least one energy output at which the ultrasound/HF instrument is connectable. In order to provide a surgical device which is improved for using an ultrasound HF instrument the surgical device includes a protective device which operatively prevents sparks generated by HF energy or reduces their probability of occurrence.

The protective device of the surgical device can include a HF voltage limiter which prevents a HF output voltage above a above a predetermined HF threshold voltage at the HF outputs within a response time of less than 1 ms.

The invention also relates to a combined surgical ultrasound HF instrument for cutting and/or coagulating biological tissue, including at least one HF electrode through which HF energy is introducible into the tissue and including an ultrasound converter which operatively converts an electrical excitation signal into ultrasound vibrations, wherein the ultrasound vibrations are introducible through the ultrasound HF instrument into biological tissue for cutting and/or coagulating tissue. In order to provide an improved combined instrument the instrument includes a protective device which prevents sparks operatively generated by HF energy or reduces the probability of occurrence of the sparks.

In an preferred embodiment of the instrument the protective device can include a HF voltage limiter which prevents a HF voltage above a predetermined threshold voltage at the HF electrodes within an response time of less than 1 ms.

Subsequently the invention is described with reference to preferred embodiments with features which can be combined at will and which are illustrated in drawing figures, wherein.

Initially, the ultrasound and HF surgical system according to the invention shall be described with reference to the embodiment according to FIG. 1.

Figure 1:
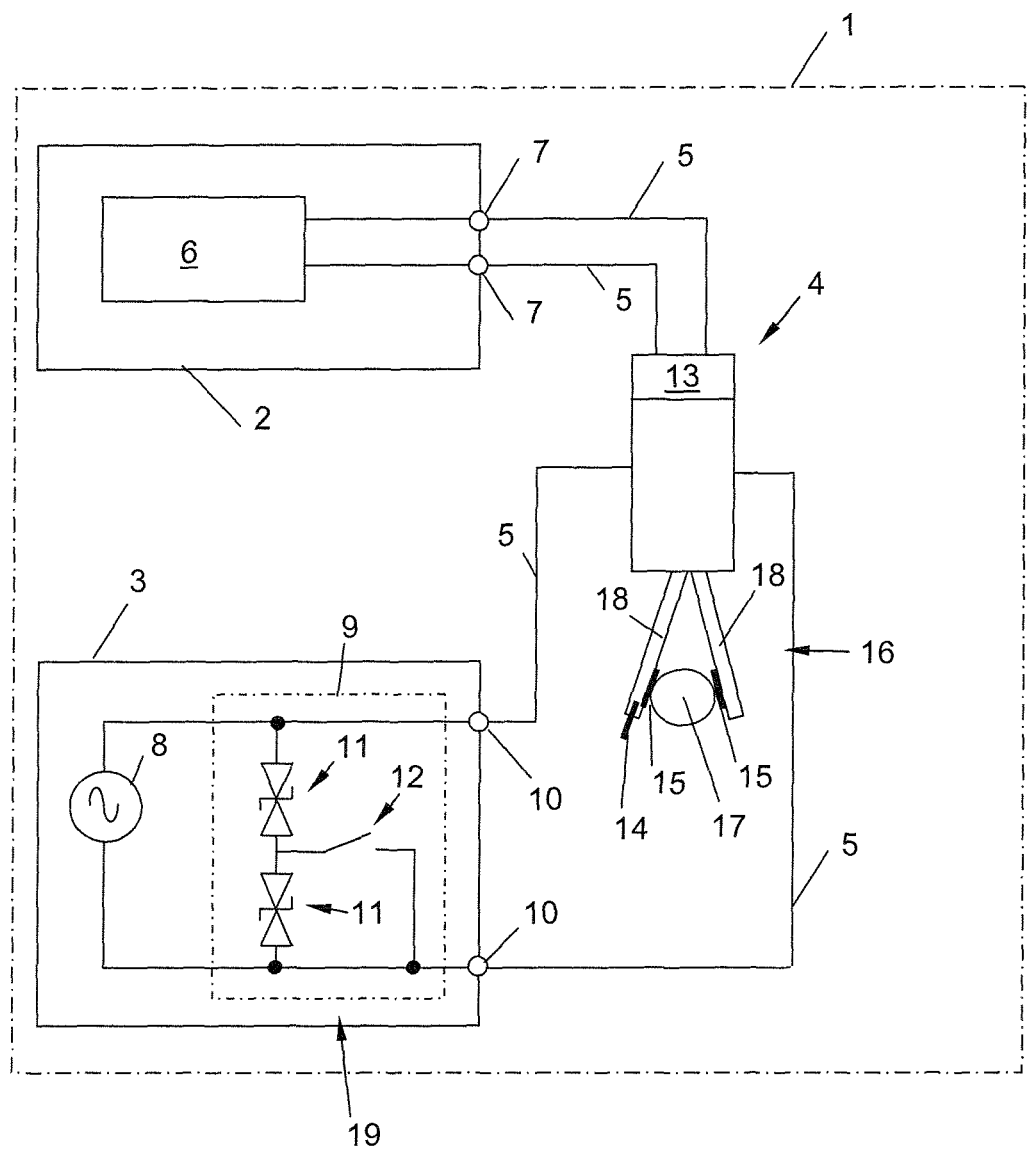
FIG. 1 illustrates a schematic view of a first embodiment of a system according to the invention.

FIG. 1 illustrates a combined ultrasound and HF surgical system 1 with an ultrasound generator 2, a HF generator 3 and a combined ultrasound and HF instrument 4 which is electrically connected with the HF generator 3 and also with the ultrasound generator 2 through connecting leads 5.

The ultrasound generator 2 includes a generation unit 6 for an excitation signal and output contacts 7 electrically connected with the generation unit 6. The generation unit 6 operatively provides an electrical excitation signal through which an ultrasound converter can generate an ultrasound vibration. Thus, the excitation signal is an AC power signal with a frequency of approximately 46-48 kHz. Alternatively the excitation signal can be in a range between 35 and 50 kHz. The excitation signal is provided at the output contacts 7 of the ultrasound generator 2. The output contacts can certainly also be disposed within a common output socket.

In the embodiment in FIG. 1 the HF generator 3 includes a HF AC power source 8, a voltage limiter 9 and two HF output contacts 10. The HF AC power source 8 and the voltage limiter 9 are thus electrically connected with the two HF output contacts 10. Thus, the HF AC power source 8 and the voltage limiter 9 are connected in parallel with one another.

The HF power source operatively generates HF energy optimized in a known manner for cutting and/or coagulating biological tissue. This HF energy is provided at both HF contacts 10 with a different polarity.

The voltage limiter 9 includes two bidirectional TVS diodes 11 connected in series and a switch 12 in the embodiment illustrated in FIG. 1. The switch 21 configured in FIG. 1 as a closing switch is disposed as a shunt about one of the two TVS diodes 11. Any suitable switching device can be used as a switch 12 e.g. a relay.

The HF generator 3 and the ultrasound generator 3 include an operating mode optimized for combined ultrasound and HF application, wherein output signals optimized for the combined application are provided in the optimized operating mode.

The ultrasound/HF instrument 4 illustrated in FIG. 1 in a highly simplified manner includes an ultrasound converter 13, an ultrasound applicator 14 and two HF electrodes 15. The ultrasound converter 13 is electrically connected on one side with the output contacts 7 of the ultrasound generator 2 through the connecting leads 5 and on the other side mechanically connected with the ultrasound applicator 14 (not illustrated). The ultrasound applicator 14 is configured rod shaped and extends from a proximal end where it is connected with the ultrasound convertor 13 to the distal end of the instrument 4.

The distal end of the instrument 4 is configured in the embodiment according to FIG. 1 as a tissue gripper 16 which facilitates gripping the tissue 17 to be treated. The gripper 16 includes two gripper arms 18 between which the tissue 17 can be gripped and retained. A HF electrode 15 is disposed at each gripper arm 18, so that the respective electrode contacts the gripped tissue 17. The HF electrodes 15 are respectively connected with one of the HF output contacts 10 (not illustrated). The ultrasound applicator 14 is integrated in one of the gripper arms 18, so that it also contacts the gripped tissue 17. In order to provide insulation, an insulation element e.g. made from Teflon is disposed between the ultrasound applicator 14 and the HF electrode 15. Furthermore a coating (not illustrated) can be applied to the ultrasound applicator 14.

When using the combined ultrasound and HF surgical system 1 illustrated in FIG. 1 the tissue 17 is gripped with the gripper 16.

For the ultrasound application the ultrasound generator 2 initially provides the excitation signal which is passed on to the ultrasound convertor 13 of the instrument 4. The ultrasound converter 13 converts the electrical excitation signal into a mechanical ultrasound vibration. The ultrasound vibration is transmitted by the ultrasound convertor 13 to the ultrasound applicator 14. The ultrasound applicator conducts the ultrasound vibration further to the distal end of the instrument 4 where it is applied to the tissue 17. For the embodiment in FIG. 1 the ultrasound vibration is used e.g. for cutting the tissue 17.

For the HF application through the system 1 the HF generator 2 generates HF energy, thus a high frequency AC power signal with a frequency between 300 kHz and 2 MHz. From the HF output contacts 10 the HF energy is conducted to the HF electrodes 15 of the instrument 4. The HF energy is conducted into the tissue 17 through the HF electrodes 15 e.g. to cause a coagulation of the tissue.

For the combined ultrasound and HF instrument 4 the ultrasound application and the HF application are combined with one another. Thus, the gripped tissue 17 can e.g. be coagulated through the HF energy and can simultaneously be cut through the ultrasound energy.

It is known that the HF energy can operatively create sparks or arcing between the HF electrodes 15 or between the tissue 17 and one of the HF electrodes 15. For a pure HF instrument the sparks are rather non-problematic compared to an ultrasound instrument. However, for a combined ultrasound and HF instrument it has become apparent that components important for ultrasound application like e.g. an insulating element or a coating (both not illustrated) can be damaged or even destroyed through long lasting high energy HF sparks. In the system 1 according to the invention such sparks caused by HF energy are prevented by a protective device 19.

Figure 2:
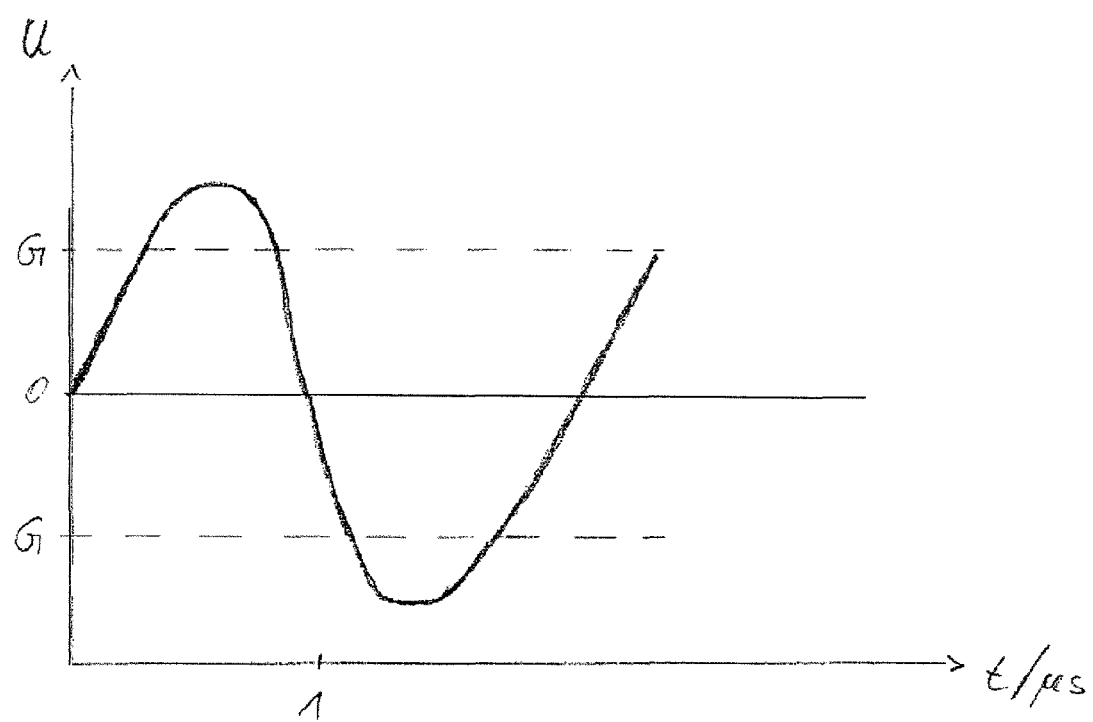
FIG. 2 illustrates a schematic voltage diagram.

The HF voltage plays a decisive role for the creation of sparks and arcs from HF energy. FIG. 2 illustrates a voltage diagram as generated e.g. by the AC current source 8 of FIG. 1. The illustrated HF energy signal thus has a frequency of approximately 500 kHz. It has become apparent that only a HF voltage above a particular threshold voltage G can generate a spark. No spark is generated by HF voltages below the threshold voltage or the probability of occurrence is significantly reduced.

Figure 3:
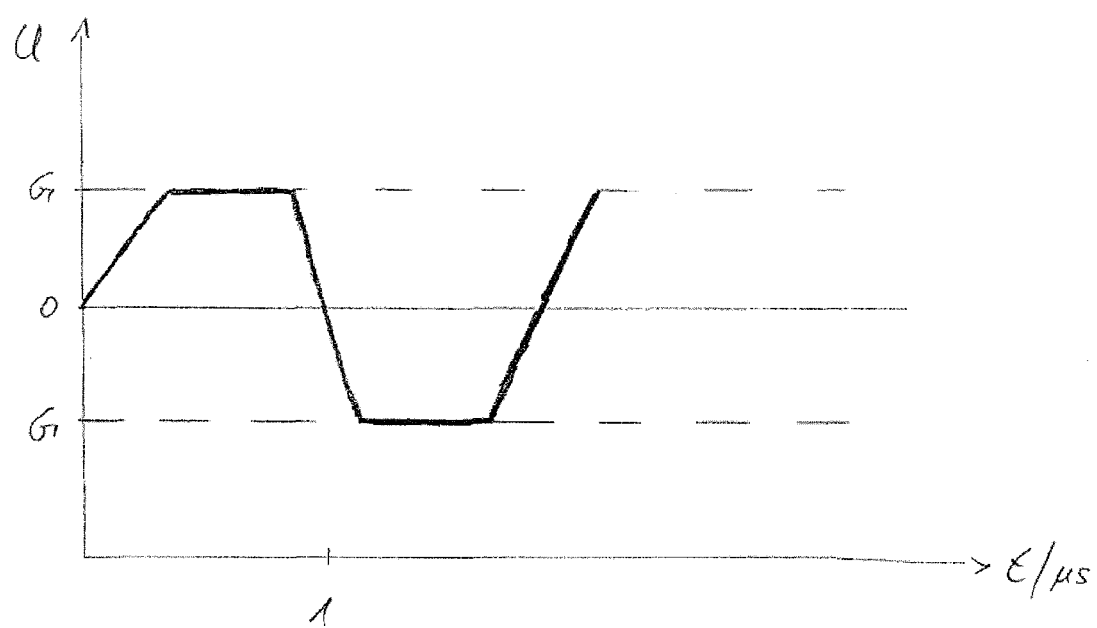
FIG. 3 illustrates a schematic voltage diagram.

FIG. 3 illustrates a voltage diagram of the HF energy as operatively provided at the output contacts 10 of the HF generator 3 in FIG. 1. Thus, a HF voltage above the threshold voltage G is prevented by the voltage limiter 9. At the most, the HF voltage at the HF output contacts 10 is limited to the threshold voltage G. The response time of the voltage limiter 9 is thus below 1 μs. Thus, a formation of sparks or arcs at the HF electrodes 15 is excluded. Even in case a spark was created within the response time of the voltage limiter 9, the spark would have such low energy until the voltage limiter responds, so that the spark would have no effect.

For the described limiting of the HF output voltage, the voltage limiter 9 in FIG. 1 includes two TVS diodes 11 connected in series. Each of the two TVS diodes herein has a particular threshold voltage, which is approximately half of the threshold voltage G. Thus, the threshold voltage G of the voltage limiter 9 is adjusted by two TVS diodes connected in series. Thus, the threshold voltage G in the embodiment of FIG. 1 is e.g. 200 volts. The voltage limiter blocks for voltages below the threshold voltage G, this means it is essentially ineffective. Only for voltages above the threshold voltage G, the voltage limiter becomes conductive and conducts the damaging energy portion above the threshold voltage G out through the TVS diodes. Thus, it is advantageous in particular, that the output voltage is continuously provided at the HF output contacts 10 and the instrument 4 can continuously be operated also in a limiting case.

The switch 12 can be used to change the threshold voltage G of the voltage limiter 9. When the switch 12 is closed, only one TVS diode 11 is still active in the voltage limiter 9, so that the threshold voltage G is reduced to half. Thus, the threshold voltage G can be adjusted e.g. for different applications or operating modes of the system 1 according to the invention.

Subsequently, another embodiment of the ultrasound and HF surgical system according to the invention is illustrated with reference to FIG. 4. For the sake of simplicity, only the differences over the embodiment in FIG. 1 are recited.

Contrary to the embodiment in FIG. 1, the ultrasound generator 2 in FIG. 2 additionally includes two HF energy outputs 20 and two HF energy inputs 21. The HF energy inputs 21 are electrically connected with the HF output contacts 10 of the HF generator 3. The HF electrodes 15 of the instruments 4 are connected to the energy outputs 20. Thus, the instrument is only connected with one unit, namely the ultrasound generator 2. This has the advantage that handling the instrument 4 is simplified for a user and the connecting leads 5 can be integrated into a joint cable. Furthermore, providing the HF energy to the instrument 4 is centrally controlled through a control device (not illustrated) of the ultrasound generator 2. This has the advantage that a central unit, thus the ultrasound generator 2, controls the combined ultrasound and HF surgical instrument 4. The HF generator can certainly also form the central unit in an alternative embodiment and can control the excitation signal for the instrument 4.

Figure 4:
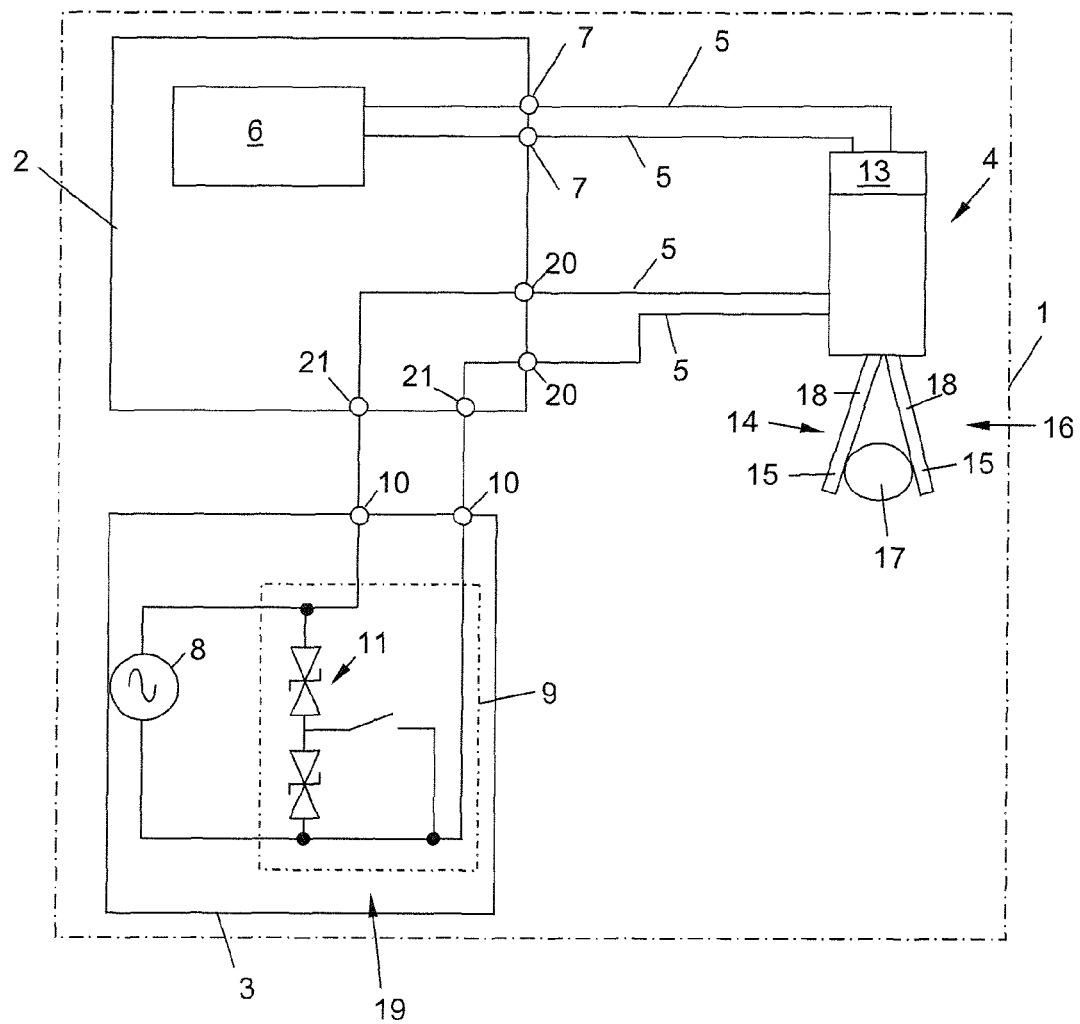
FIG. 4 illustrates a schematic view of another embodiment of the system according to the invention.

Furthermore, the gripping arms 18 are made from electrically conductive material for the embodiment in FIG. 4. They are connected with the energy outputs 20, and form the HF electrodes 15. A gripping arm 18 simultaneously forms the ultrasound applicator 14 at least partially.

Figure 5:
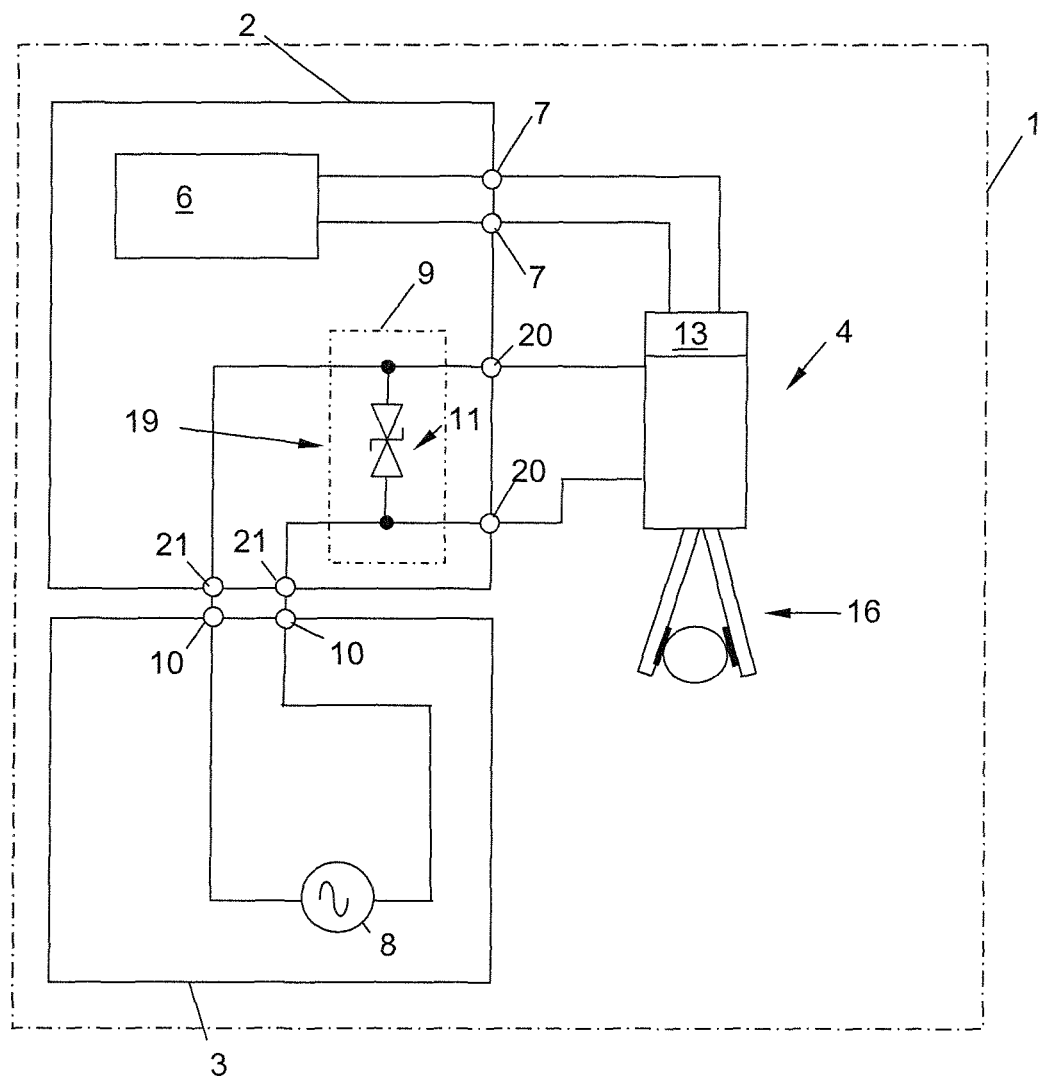
FIG. 5 illustrates a schematic view of another embodiment of the system according to the invention.

Subsequently, another embodiment of the ultrasound and HF surgical system is illustrated with reference to FIG. 5. For simplicity reasons, only the differences over the embodiment in FIG. 4 are recited.

Differently from the embodiment in FIG. 4, the voltage limiter 9 is disposed in the ultrasound generator 2. Thus, the voltage limiter 9 is connected parallel to the HF energy outputs 20. Contrary to the preceding embodiments, the voltage limiter 9 in FIG. 5 only includes one TVS diode 11 and no switch 12. The threshold voltage G is thus fixated.

Subsequently, another embodiment of the ultrasound and HF surgical system according to the invention is illustrated with reference to FIG. 5. For simplicity reasons, only the differences over the embodiment in FIG. 4 are described.

Contrary to the embodiment in FIG. 4, the voltage limiter 9 is disposed in the instrument 4. Thus, the voltage limiter 9 is connected parallel to the HF electrodes 15.

Subsequently, another embodiment of the ultrasound and HF surgical system is illustrated with reference to FIG. 6. For reasons of simplicity, only the differences over the preceding embodiments are described.

Figure 6:
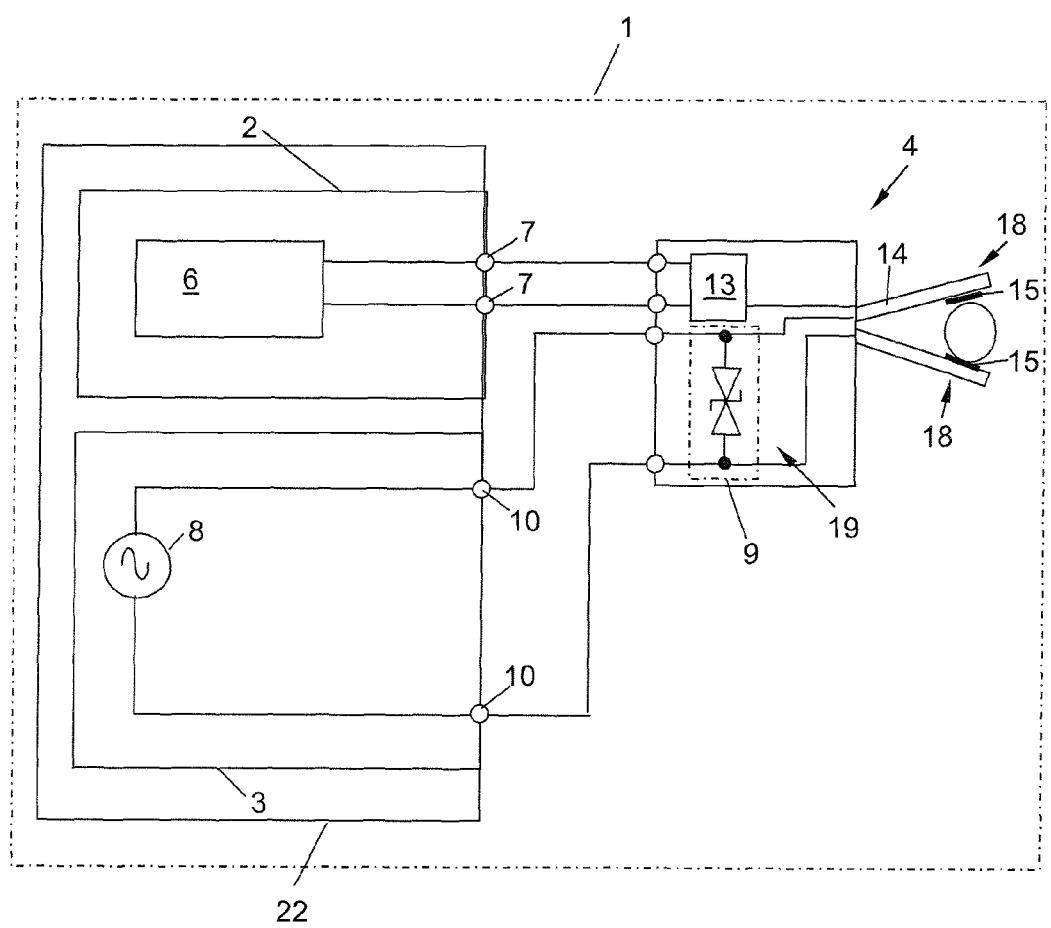
FIG. 6 illustrates a schematic of a further embodiment of the system according to the invention.

In the embodiment in FIG. 6, the HF generator 3 and the ultrasound generator 2 are integrated into a combined ultrasound and HF generator 22 at which the instrument 4 is connected.

Contrary to the preceding embodiments, the voltage limiter 9 is disposed in the combined instrument 4, thus between the HF electrodes 15.

Additional embodiments of the invention are certainly feasible. Furthermore, the voltage limiter 9 can be disposed at any location in the energy path of the HF energy, like e.g. in a connector of the instrument 4 or in a separate connection lead 5.

The invention claimed is:

1. A combined ultrasound and HF surgical system, comprising:
   at least one ultrasound generator which operatively provides an excitation signal;
   at least one HF generator which operatively generates HF energy;
   at least one ultrasound and HF instrument electrically connected with the HF generator and the ultrasound generator, the ultrasound and HF instrument including at least one ultrasound converter and at least one HF electrode wherein:
      the ultrasound generator operatively provides the excitation signal through which the ultrasound convertor can generate an ultrasound vibration;
      the ultrasound vibration and the HF energy are introducible into biological tissue through the ultrasound and HF instrument; and a protective device which prevents sparks operatively generated by the HF energy or reduces the probability of occurrence of the sparks, wherein:
the protective device includes a HF voltage limiter which prevents a HF voltage above a predetermined threshold voltage between a first HF electrode and a second HF electrode of the at least one HF electrode within a response time of less than 1 ms,
the HF voltage limiter includes at least a TVS diode, and
the TVS diode is configured to reduce the HF voltage to the predetermined threshold voltage and to conduct out a damaging energy portion through the TVS diode.

2. The system according to claim 1, wherein the HF voltage limiter prevents the HF voltage above the predetermined threshold voltage within the response time of less than 1 µs.

3. The system according to claim 1, wherein the HF voltage limiter includes at least one switch configured to switch between at least two different threshold voltages.

4. The system according to claim 1, wherein the HF voltage limiter is electrically connected between the HF electrodes.

5. A HF generator for generating HF energy for cutting and/or coagulating biological tissue, comprising:
at least two HF outputs with different polarities, at which HF electrodes of a surgical ultrasound and HF instrument are connectable, wherein the HF generator has at least one ultrasound/HF operating mode, in which a HF output energy optimized for the ultrasound and HF instrument is provided at the HF outputs: and
a protective device which prevents sparks operatively generated by the HF output energy or reduces their probability of occurrence, wherein:
the protective device includes a HF voltage limiter which prevents a HF voltage above a predetermined threshold voltage at the HF outputs within a response time of less than 1 ms,
the HF voltage limiter includes at least a TVS diode, and
the TVS diode is configured to reduce the HF voltage to the predetermined threshold voltage and to conduct out a damaging energy portion through the TVS diode.

6. A surgical device for providing an ultrasound energy signal and an HF energy signal for cutting and/or coagulation biological tissue, comprising:
an ultra-sound generator which operatively provides an excitation signal, through which an ultrasound converter can generate an ultrasound vibration;
at least one ultrasound output connected with the ultrasound generator, wherein an ultrasound and HF instrument is connectable at the ultrasound output;
at least one HF energy input, at which a HF generator is connectable for introducing a HF energy signal;
at least one energy output, at which the ultrasound and HF instrument is connectable; and
a protective device, which prevents sparks operatively generated by the HF energy signal or reduces the probability of occurrence of the sparks, wherein:
the protective device includes a HF voltage limiter which prevents a HF voltage above a predetermined threshold voltage at HF energy outputs of the at least one energy output within a response time of less than 1 ms,
the HF voltage limiter includes at least a TVS diode, and
the TVS diode is configured to reduce the HF voltage to the predetermined threshold voltage and to conduct out a damaging energy portion through the TVS diode.

7. A surgical ultrasound and HF instrument for cutting and/or coagulating biological tissue, comprising:
at least one HF electrode, through which HF energy is introducible into a tissue;
an ultrasound converter, which operatively converts an electrical excitation signal into ultrasound vibrations, wherein the ultrasound vibrations are introducible through the ultrasound and HF instrument into biological tissue for cutting and/or coagulating the tissue; and
a protective device which prevents sparks operatively generated through HF energy or reduces the probability of occurrence of the sparks, wherein:
the protective device includes a HF voltage limiter which prevents a HF voltage above a predetermined threshold voltage between a first HF electrode and a second HF electrode of the at least one HF electrode within a response time of less than 1 ms,
the HF voltage limiter includes at least a TVS diode, and
the TVS diode is configured to reduce the HF voltage to the predetermined threshold voltage and to conduct out a damaging energy portion through the TVS diode.

* * * * *